(12) United States Patent
Lee et al.

(10) Patent No.: US 6,416,652 B1
(45) Date of Patent: Jul. 9, 2002

(54) METHOD FOR MEASURING AMMONIA IN BIOCHEMICAL PROCESSES

(75) Inventors: Jaw Fang Lee, Berwyn; Sergey K. Maneshin, Upper Holland; Marcus E. Kolb, Phoenixville; Xin Yang, Holland, all of PA (US)

(73) Assignee: Bio Chem Technology, Inc., PA (US)

( * ) Notice: Subject to any disclaimer, the term of this patent is extended or adjusted under 35 U.S.C. 154(b) by 159 days.

(21) Appl. No.: 09/618,899

(22) Filed: Jul. 18, 2000

Related U.S. Application Data

(62) Division of application No. 09/136,105, filed on Aug. 18, 1998, now Pat. No. 6,143,246.

(51) Int. Cl.$^7$ ............................................... G01N 27/26
(52) U.S. Cl. .................................... 205/780.5; 205/775
(58) Field of Search ............................. 205/775, 780.5, 205/787

(56) References Cited

U.S. PATENT DOCUMENTS

| | | | |
|---|---|---|---|
| 3,348,409 A | 10/1967 | Arthur | |
| 3,354,057 A | 11/1967 | Klingelhoefer | |
| 3,374,065 A | 3/1968 | Suzuki | |
| 3,565,583 A | 2/1971 | McNulty et al. | |
| 3,616,273 A | 10/1971 | Oita | |
| 3,877,875 A | 4/1975 | Jones et al. | |
| 4,162,195 A | 7/1979 | Solyom et al. | |
| 4,209,299 A | 6/1980 | Carlson | |
| 4,216,065 A | 8/1980 | Rechnitz et al. | |
| 4,220,715 A | 9/1980 | Ahnell | |
| 4,277,343 A | 7/1981 | Paz | |
| 4,288,229 A | 9/1981 | Mar | |
| 4,297,173 A | 10/1981 | Hikuma et al. | |
| 4,666,610 A | 5/1987 | Kuhns | |
| 4,700,709 A | 10/1987 | Kraig | |
| 4,845,025 A | 7/1989 | Lary et al. | |
| 5,013,442 A | 5/1991 | Davis et al. | |
| 5,389,524 A | 2/1995 | Larsen et al. | |
| 5,401,412 A | 3/1995 | Yang et al. | |
| 5,466,604 A | 11/1995 | Yang et al. | |
| 5,552,319 A | 9/1996 | Yang et al. | |
| 5,629,202 A | 5/1997 | Su et al. | |
| 5,641,966 A | 6/1997 | Karlberg et al. | |
| 5,658,802 A | 8/1997 | Hayes et al. | |
| 5,698,412 A | 12/1997 | Lee et al. | |
| 5,702,951 A | 12/1997 | Bridger | |
| 5,882,937 A | 3/1999 | Sauer | |

FOREIGN PATENT DOCUMENTS

| | | |
|---|---|---|
| DE | 38 11 540 A1 | 10/1989 |
| EP | 0 414 182 A1 | 2/1991 |
| EP | 0 531 955 A2 | 3/1993 |
| JP | 52-64992 | 5/1977 |
| JP | 58-52558 | 3/1983 |
| JP | 58-187850 | 11/1983 |
| JP | 59-99353 | 6/1984 |
| JP | 8-299988 | 11/1996 |
| WO | WO 97/26525 | 7/1997 |

OTHER PUBLICATIONS

Chemical Abstracts, 11–Mammalian Biochemistry, vol. 68, 1968, p. 6465, 67110h, *An Analysis of the Nonenzymic Ammonia Production from Glutamine*, D.J. O'Donovan Month Unknown.

Analyst, Sep. 1975, vol. 100, pp. 620–628, *Determination of Ammonia–, Nitrate–and Organic Nitrogen in Water and Waste Water with an Ammonis Gas–Sensing Electrode*, L.R. McKenzie et al.

(List continued on next page.)

*Primary Examiner*—T. Tung
*Assistant Examiner*—Alex Noguerola
(74) *Attorney, Agent, or Firm*—Schnader Harrison Segal & Lewis LLP

(57) ABSTRACT

The present invention relates to apparatus and a method for measuring ammonia in biochemical processes, and more particularly to apparatus for real time measuring the amount of ammonia in a liquid with or without suspended solids.

13 Claims, 13 Drawing Sheets

OTHER PUBLICATIONS

Analytica Chimica Acta, 92(1977), pp. 277–283, *A New pH Electrode for Gas–Sensing Probes*, M. Mascini et al. Month Unknown.

Anal. Chem., Oct. 1982, 54, pp. 2085–2089, *Selectivity of the Potentiometric Ammonia Gas Sensing Electrode*, M.E. Lopez et al.

Month Unknown Aqua No. 6, 1983, pp. 292–297, *New Instrumentation in Automatic Water Quality Monitoring*, T. Kohonen et al.

Month Unknown Analytica Chimica Acta, 214(1988) pp. 367–374, *Applications of flow injection Analysis in a Power Plant Determination of pH, Ammonia and Hydrazine in an AVT–Conditioned Water Steam Cycle*, M.L. Balconi et al.

Month unknown Toxicity Assessment: An International Journal, vol. 4, (1989), pp. 85–104, *Anaerobic Subsurface Soil Microcosms: Methods to Monitor Effects of Organic Pollutants on Indigenous Microbial Activity*, J. M. Dougherty et al.

Month unknown Analytica Chimica Acta, 234 (1990), pp. 167–173, *Flow–Injection Analysis for Power Plants: Evaluation of Detectors for the Determination of Control Parameters in Conditioned Water–Steam Cycles*, M.L. Balconi et al.

Month unknown Analytica Chimica Acta, 237 (1990), pp. 115–125, *Differential Ion–Selective Membrane Electrode-Based Potentiometric Gas–Sensing Cells with Enhanced Gas Sensitivity*, H.S. Yim et al.

Month unknown Research Journal WPCF, vol. 63, No. 3, May/Jun. 1991, pp. 208–219, *Effects of Oxygen Transport Limitation on Nitrification in the Activated Sludge Process*, M.K. Stenstrom et al.

Month unknown Wat. Sci. Tech., vol. 25, No. 6, 1992, pp. 43–57, *Characterization of Functional Microorganism Groups and Substrate in Activated Sludge and Wastewater by AUR, NUR and OUR*, G.H. Kristensen et al.

Month unknown Chemical Abstracts, vol. 118, 1993, p.464, 108921v, *Anaerobic–Aerobic Treatment of High–Strength Ammonium Wasterwater–Nitrogen Removal Via Nitrite*, J. Abeling et al.

Month unknown Operations Forum, Feb. 1994, pp. 8–11, *Alkalinity Tells All: Real–Time Control for the Entire Process*, A.J. Freed et al.

Analyst, vol. 119, Aug. 1994, pp. 1839–1842, *Continuous-Flow System for the Accurate Determination of Low Concentrations of Ammonium Ions Using a Gas–Permeable Poly(tetrafluoroethylene) Tube Decontaminator and an Ammonia Gas–Sensing Membrane Electrode*, H. Hara et al., Aug.

Journal of Automatic Chemistry, vol. 16, No. 5 (Sep.–Oct. 1994), pp. 153–154, *Environmental Monitoring–A Flow–Injection Approach*, P.J. Worsfold Month unknown.

Wat. Sci. Tech., vol. 31, No. 7, 1995, pp. 181–189, *Aerobic Biodegradation and Microbial Population of a Synthetic Wastewater in a Channel With Suspended and Attached Biomass*, Y.S. Cao et al. Month unknown.

Analyst, vol. 122, Jan. 1997, pp. 89–93, *Determination of Ammonia in Waste Waters by a Differential pH Method Using Flow Injection Potentiometry and a Nonactin–Based Sensor*, H. Shen et al.

Wat. Sci. Tech., vol. 35, No. 1, 1997, pp. 57–66. *Monitoring and Control Using On–Line ORP on the Continuous–Flow Activated Sludge Batch Reactor System*, R–F Yu et al. Month unknown.

Month unknown LRA, vol. 9, 1997, pp. 175–183, *In Situ Flow–Injection Monitoring of Ammonia in Landfill Leachate*, M.J. Bloxham et al. Month unknown.

METHOD FOR MEASURING AMMONIA IN BIOCHEMICAL PROCESSES

This application is a divisional of Ser. No. 09/136,105, filed Aug. 18, 1998, which is now U.S. Pat. No. 6,143,246.

FIELD OF THE INVENTION

The present invention relates to an apparatus and a method for measuring ammonia in liquid and controlling the treatment thereof, more particularly, to apparatus for real time measuring the amount of ammonia in liquid with or without suspended solids in a biochemical process and using the results of such measuring to control selected aspects of the process.

BACKGROUND OF THE INVENTION

The prior art has employed many devices and systems to process and purify water from industrial operations and municipal sources prior to discharging the water. Wastewater treatment plants (WWTP's), which are well known in the art, have been most often utilized to address this problem. Additionally, many industrial and municipal water treatment plants utilize biological systems to pre-treat their wastes prior to discharging into the usual municipal treatment plant.

Microorganisms used in the sludge break down or degrade contaminants for the desired water treatment in these processes. Efficient process performance and control requires quick and accurate assessment of information on the activity of the microorganisms. This has proven to be a difficult task in view of the wide variety of materials and contaminants that typically enter into treatment systems. Also, variations in the quantity of wastewater being treated, such as daily, weekly or seasonal changes, can dramatically change numerous important factors in the treatment process, such as pH, temperature, dissolved oxygen, nutrients and the like, alteration of which can be highly detrimental to proper wastewater treatment. Improperly treated wastewater poses serious human health dangers.

Various biological nutrient removal (BNR) processes are often used in biochemical systems/plants/processes. "BNR" is used hereinafter in a very generic sense, namely any biochemical process that uses microorganisms to remove nutrients. In BNR processes, contaminants in liquids such as wastewater, particularly carbon sources (measured as biochemical oxygen demand or BOD), ammonia, nitrates, phosphates and the like are digested by activated sludge in anaerobic, anoxic and aerobic (oxic) stages, also known in the art. In the anaerobic stage, wastewater, with or without passing through a preliminary settlement process, is mixed with return activated sludge (RAS), sometimes hereinafter referred to as "mixed liquor."

It is, of course, important to quantify the various contaminants in the wastewater. One of those contaminants that is important to quantify is the amount of ammonia. This is because quantification of the amount of ammonia provides valuable information about nitrification/dentrification processes, for example. Various system parameters such as retention time can be altered to enhance the process and increase treatment system efficiency in response to this important information.

A wide variety of methods have been attempted to measure the amount of ammonia in wastewater. However, there have been a number of serious drawbacks in obtaining accurate ammonia quantities on a real time basis. One significant drawback has been the need to filter wastewater samples prior to measuring the amount of ammonia. This is a severe constraint on the real time ability to obtain accurate ammonia readings. Prior art known to the inventors includes the following U.S. Pat. Nos.: 3,354,057; 3,565,583; 3,616,273; 3,877,875; 4,162,195; 4,209,299; 4,216,065; 4,277,343; 4,297,173; 4,666,610; 5,466,604 and 5,641,966.

OBJECTS OF THE INVENTION

It is an object of the present invention to provide apparatus and a method for measuring the amount of ammonia in biochemical systems to maximize the efficiency of the treatment process.

It is a further object of the present invention to provide apparatus and a method for real-time measuring of the amount of ammonia in liquids to enhance control of the biochemical process, to maximize process performance in response to transient and other conditions.

Other objects of the present invention will be apparent to those of ordinary skill in the art based on the following drawings, detailed description of preferred embodiments and the appended claims.

SUMMARY OF THE INVENTION

One aspect of the invention includes apparatus for measuring ammonia in liquids, especially wastewater. It includes a wastewater sample container having a fluid flow opening connected to a fluid supply; optionally, a pH probe positioned to detect the pH of samples in the container and an ammonia probe positioned to detect ammonia in the samples. A pH adjustment supply connects to the container and an ammonia adjustment supply connects to the container. Optionally, a pH analyzer is adapted to determine changes in sample pH and an ammonia analyzer is adapted to determine changes in the quantity of ammonia in the samples. A controller connects to 1) the pH adjustment supply to introduce pH adjustment solution into the container, 2) the ammonia adjustment supply to introduce ammonia adjustment solution into the container to periodically calibrate the ammonia probe, 3) the container to introduce samples into and remove samples from the container at selected time intervals, and 4) the optional pH analyzer and the ammonia analyzer to measure ammonia in the samples.

The invention also includes a method of measuring ammonia in liquids, especially wastewater. This method is different from other ammonia analyzing techniques in that there is no need to prepare the sample by filtration or other method of solids removal. The presence of organic solids in the liquid, at an elevated pH, can cause a release of ammonia to the liquid as proteinaceous compounds are hydrolyzed. This ammonia release phenomenon affects the accuracy of the ammonia measurement if not properly addressed. The invention uses a method to determine the rate of ammonia released during the ammonia measurement and compensates for it in its measurement. The method includes isolating a wastewater sample; adjusting the pH of the sample to a predetermined level for a predetermined time interval $t_1$; recording a value of ammonia present in the sample with an ammonia selective probe: recording another value of ammonia present in the sample after another predetermined time interval $t_2$; determining ammonia concentrations in the sample at each predetermined time interval $t_1$ and $t_2$ according to the following formula:

$$[NH_3] = 10^{a \cdot mV + b}$$

wherein a and b are linear coefficients of the ammonia probe; determining the amount of released ammonia from the sample according to the following formula:

$$\frac{\Delta [NH_3]}{\Delta t} = \frac{[NH_3]_2 - [NH_3]_1}{t_2 - t_1}; \text{ and}$$

determining the ammonia concentration of the sample according to the following formula:

$$[NH_3] = [NH_3]_1 - \frac{\Delta [NH_3]}{\Delta t} \cdot t_1.$$

DETAILED DESCRIPTION OF THE INVENTION

Figure 1:
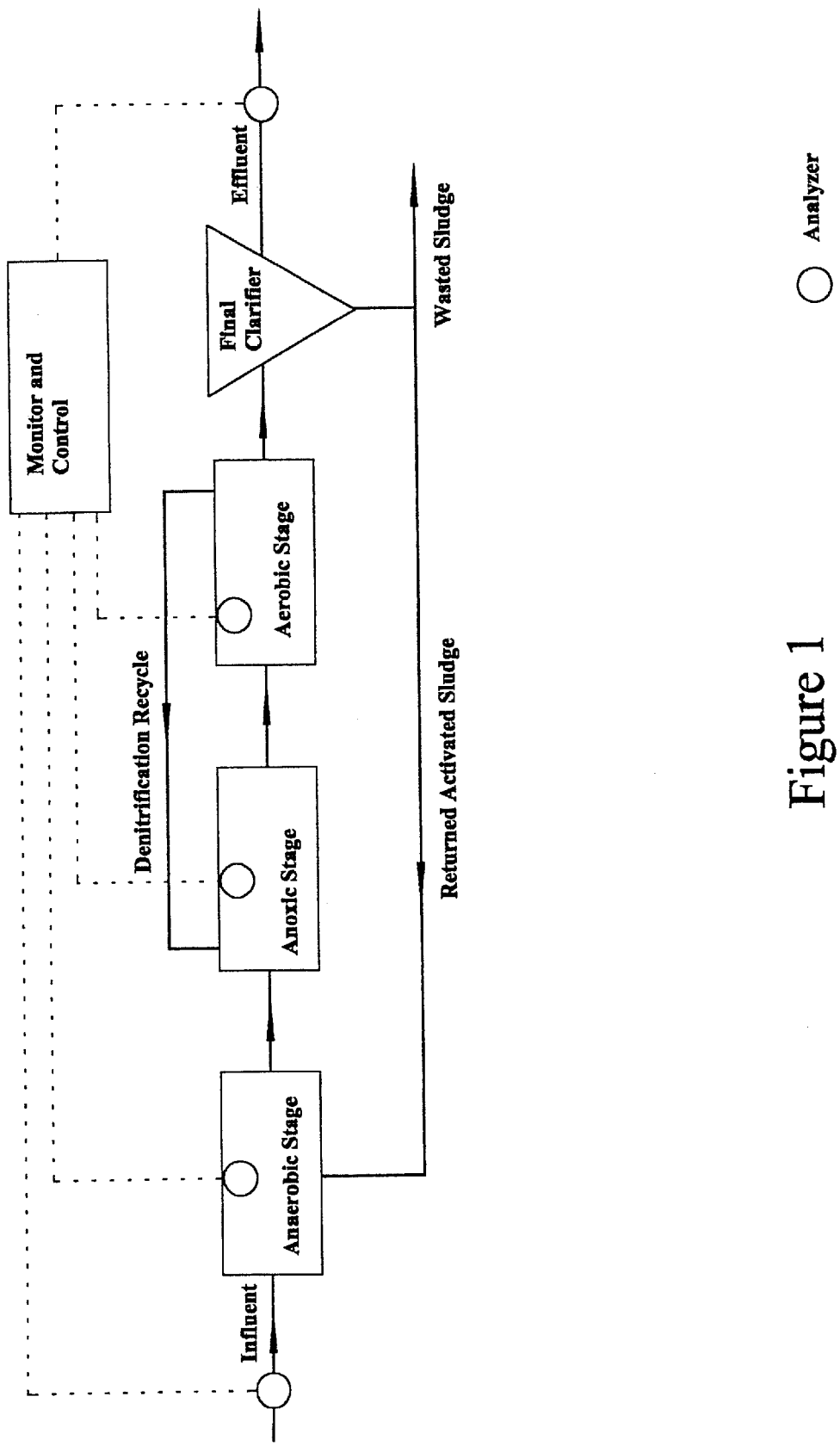
FIG. 1 is a schematic of the monitoring and control system of a typical wastewater treatment process utilizing embodiments of the invention and shows the many locations that detectors can be installed through out the system.

The following description is intended to refer to specific embodiments of the invention illustrated in the drawings and is not intended to define or limit the invention, other than in the appended claims. Also, the drawings are not to scale and various dimensions and proportions are contemplated.

In order to effectively control the operation of the BNR process, it is necessary to regulate specific process parameters based upon the biological activity of the microorganisms in the anaerobic, anoxic and/or oxic stages of the treatment. Wastewater treatment plants are often subjected to severe transient conditions, such as diurnal variations in organic loads.

The proper evaluation and control of a BNR process requires an accurate and current assessment of the amount of ammonia in the mixed liquor, among other things, in a variety of environments and under a number of conditions.

The apparatus for quantifying ammonia can be used in all stages of a WWTP or any combination thereof. Incorporation of the apparatus into a typical WWTP is shown schematically in FIG. 1. Ammonia measurements may be taken at any point or location in the system shown in FIG. 1. This includes multiple measurement locations within a selected stage, if desired. The general application and use of the apparatus in the anaerobic, anoxic and/or aerobic stages of a typical wastewater treatment plant will now be discussed.

Figure 2:
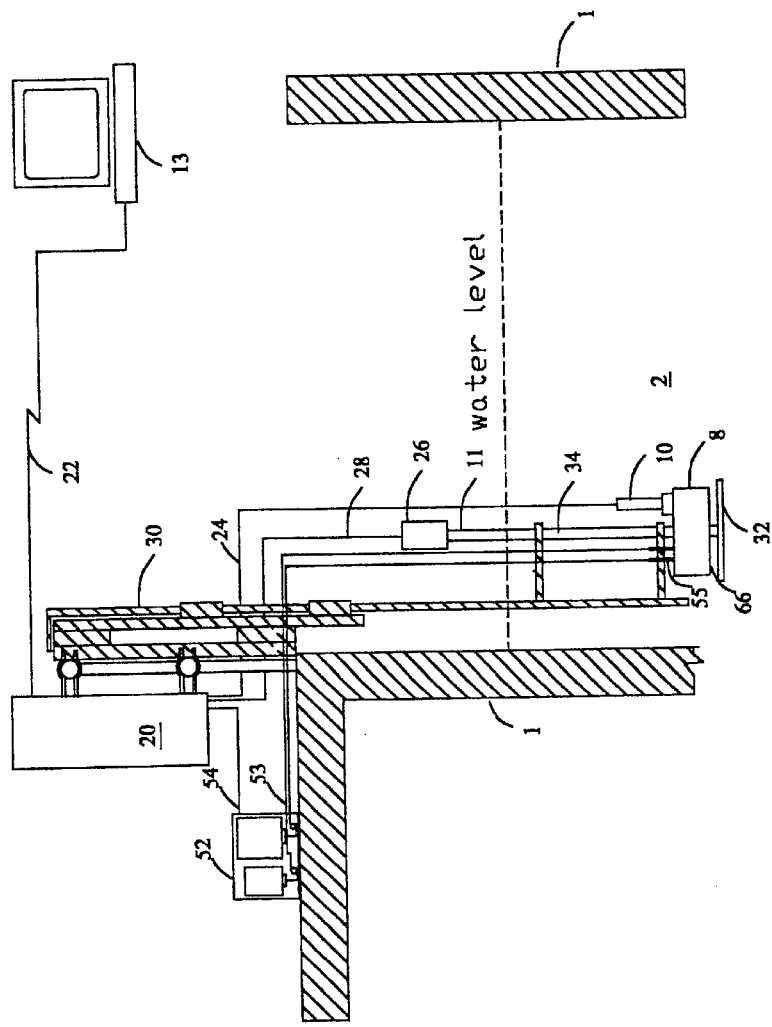
FIG. 2 shows a schematic front elevational view of an embodiment of apparatus of the invention used to monitor a bioreactor tank.
Figure 3:
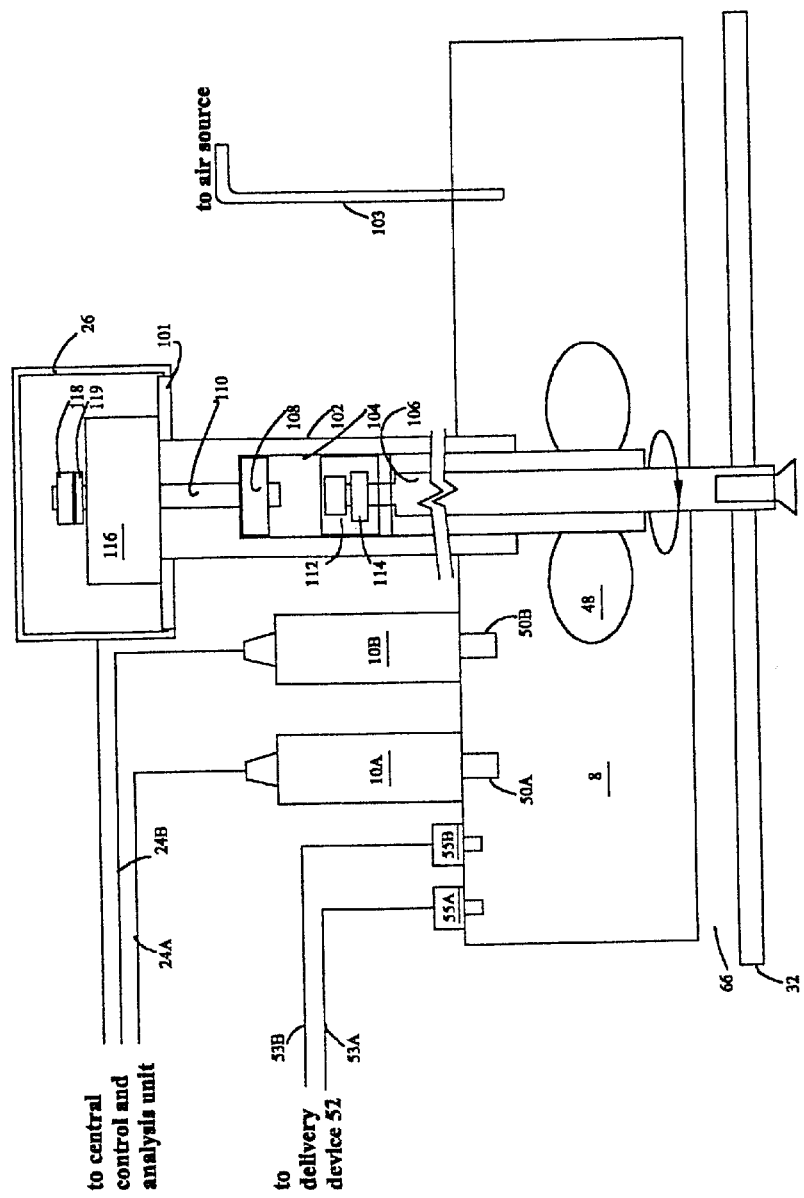
FIG. 3 shows an exploded schematic view, partially taken in section, of wastewater sampling apparatus in accordance with aspects of the invention.

One embodiment of apparatus for sampling wastewater is shown in FIGS. 2 and 3. A bioreactor tank 1 (or, alternatively, a wastewater channel) contains wastewater 2 and/or sludge. Detection apparatus is mounted on the top of bioreactor tank 1 and extends into wastewater 2. The apparatus includes a central control and analysis unit 20 connected to an optional computer/monitor 13 by wire or wireless connection 22. Similarly, central control and analysis unit 20 connects to detection probes 10A and 10B by way of wire connections 24. Motor container 26 also connects to central control and analysis unit 20 by way of connection wire 28. Power is supplied to motor container 26 also by wire connection 28.

Detection probes 10A and 10B are positioned in detection chamber 8 and electrically connected to central control and analysis unit 20 to detect changes in the quantity of ammonia and changes in pH in wastewater samples. At low pH a preferred ammonium ion detection probe 10A is an ammonium ion probe manufactured by HACH. At mid-high pH a preferred ammonia detection probe 10A is an ammonia gas probe, also manufactured by HACH. A preferred pH probe 10B is manufactured by Sensorex. Of course, other apparatus can be employed as probes so long as the same or similar detection capabilities are available.

Optional computer/monitor 13 may be of any suitable type such as a personal computer or the like. Device 52 consists of two containers (one storing ammonia calibration solution and the other storing pH adjustment solution) and a delivery device for each, for example, a pump. Device 52 is connected to central control and analysis unit 20 by wires 54. Device 52 provides ammonia calibration and pH adjustment solution to the liquid (e.g. wastewater) in detection chamber 8 by connection tube 53. The pH adjustment solution, typically a base for mid to high pH and an acid for low pH, may be selected from a wide variety of pH altering solutions. Bases include NaOH, KOH and the like. Acids include HCl, acetic acid and the like.

Sampling unit 11 is mounted onto a movable carriage 30 which is capable of moving substantially vertically upwardly and downwardly to move the detection probes into and out of wastewater 2. The precise structure of movable carriage 30 is not critical so long as the preferred capability or movability of sampling unit 11 is achieved.

Detection probes 10 have their detection ends 50A and 50B located in detection chamber 8 as shown in FIG. 3. Detection chamber 8 has an opening 66 and an adjacent movable cover 32 which moves vertically upwardly and downwardly along guide channels 34 and closes or seals opening 66.

FIG. 3 shows detection chamber 8 having a detection probe 10A with a detection end 50A. Detection probe 10A is an ammonia detection probe. Detection chamber 8 also has a detection probe 10B with a detection end 50B. Detection probe 10B is a pH probe. Detection chamber 8 further has feed ports 55A and 55B. Feed device 52 feeds pH adjustment solution into detection chamber 8 through feed port 55B. Feed device 52 feeds ammonia to detection chamber 8 through feed port 55A. Propeller 48 is located interiorly of detection chamber 8 and stirs or agitates samples when probes 10A and 10B are in operation. Cover 32 is in an open position which, when closed, covers opening 66.

Propeller 48 is connected to motor container 26 by way of a series of coaxial tubes 102, 104 and 106. An adaptor 108 and a thrust bearing sleeve 112 are contained in and attached to middle tube 104. Outside tube 102 is mounted to base 101. Adaptor 108 is attached to threaded rod 110 to either open or close cover 32 depending on motor direction of linear actuator motor 116. Middle tube 104 travels axially only if induced drag on middle tube 104 exceeds an amount of torque required for linear actuator motor 116 to turn on threaded rod 110. This drag can be induced by propeller 48 attached to middle tube 104 and/or any bushings or other hardware in contact with middle tube 104. Thrust bearing sleeve 112 holds bearing 114 which carries axial tension of central tube 106 when cover 32 is closed. Bearing 114 allows middle tube 104 to rotate independently of central tube 106 and transfers axial motion of tube 104 to central tube 106. Outside tube 102 supports both base 101 and chamber 8 while protecting the internal parts. Chamber 8 is substantially sealed to outside tube 102 and when cover 32 is pulled against chamber 8 the space inside chamber 8 is sealed.

When linear actuator motor 116 rotates in one direction threaded rod 110 travels downward, pushing cover 32 open. When nut 118 reaches thrust bearing 119, threaded rod 110 no longer travels axially and this causes middle tube 104 to substantially match the motor speed. Chamber 8 is then in an open condition and propeller 48 induces an exchange of fluid between the inside and outside of chamber 8.

When linear actuator motor 116 rotates in the opposite direction, threaded rod 110 travels upward, pulling cover 32 closed. When chamber 8 is closed, axial motion of threaded rod 110 is prevented by tension on middle tube 104. This causes middle tube 104 to rotate at the same speed as motor 116. Chamber 8 is then in a closed position so that fluid is retained inside chamber 8 while being constantly mixed by propeller 48.

Ammonia is often a main part of the contaminants in wastewater. Therefore, a fast and easy method for real-time measurement of ammonia in wastewater is highly advantageous. Conventional methods available for this procedure include the Nesslerization method, the phenate method, the titrimetric method and the ammonia-selective electrode method.

Figure 4:
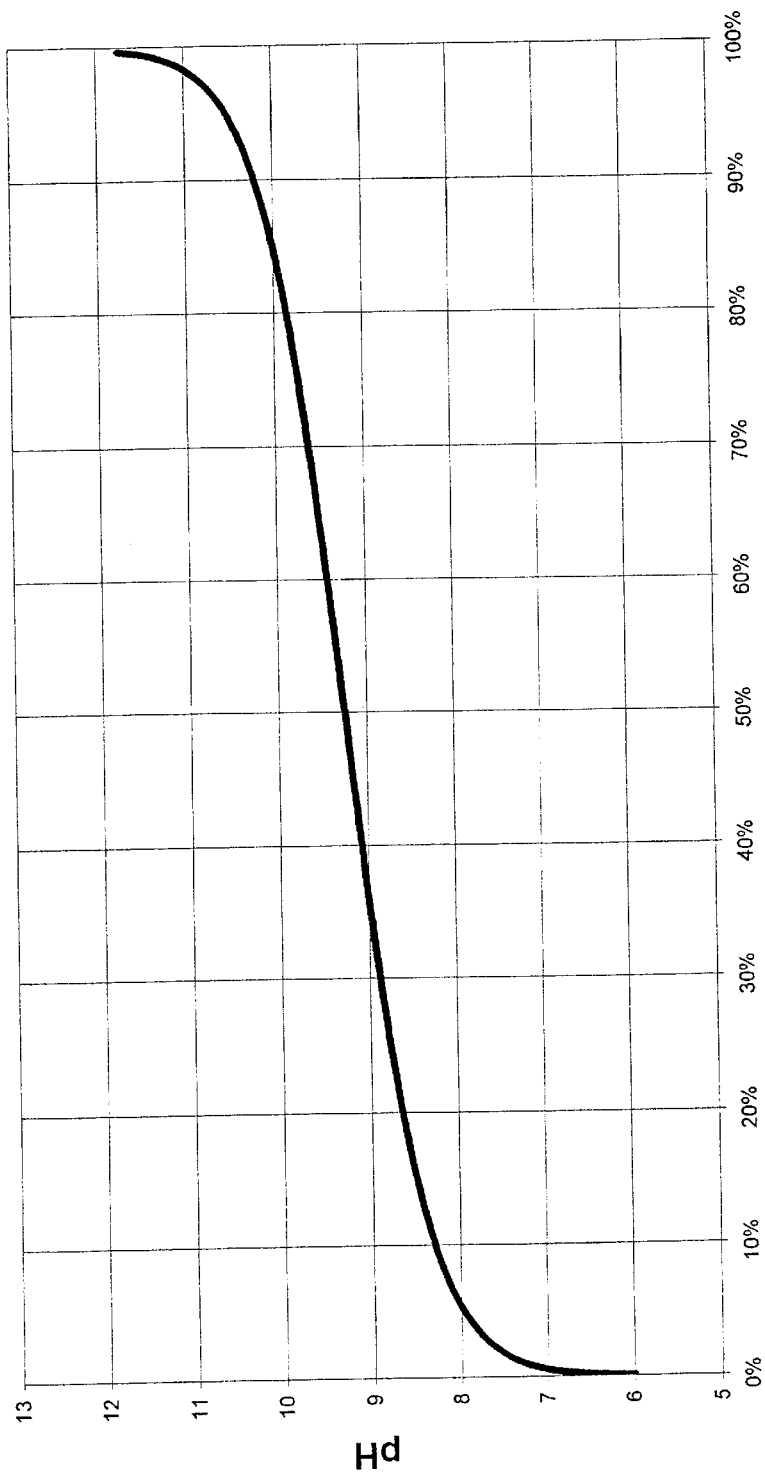
FIG. 4 is a graph of pH versus $NH_3/(NH_3+NH_4^+)$ showing equilibrium of ammonia and ammonium in an aqueous phase.

The principle for the conventional ammonia-selective electrode method is as follows. An electrode has a hydrophobic gas-permeable membrane to separate sample solution from an electrode internal solution of ammonium chloride. It is known that ammonia exists in water in two forms, as ammonium ions $NH_4$ at low pH<7 and ammonia gas form at high pH>12. At pH=9.25 the concentration of ammonia in the ions and gas is equal as shown in FIG. 4.

The conventional ammonia measurement method consists of filtration of a wastewater sample and addition of a very strong base (usually 10N KOH) to the filtered sample to convert all ammonia ions to the gas form. Ammonia gas dissolved in the aqueous phase diffuses through the membrane and changes the internal solution pH that is sensed by the pH probe. The fixed level of chloride in the internal solution is sensed by a chloride ion-selective electrode that serves as a reference electrode. Potentiometric measurements are made with a pH meter having an expanded millivolt scale or with a specific ion meter.

The invention eliminates the filtration procedure of the wastewater sample which has heretofore substantially prevented real time ammonia measurement. In the invention, pH adjustment solution or base is added to a newly isolated mixed liquor sample slowly and precisely to bring the pH to a predetermined level such as 9.25 or 12.0, for example. This predetermined value is kept constant for a selected measurement time. At pH=9.25, for example, the concentration of ammonia gas in the mixed liquor is only half of the total ammonia-nitrogen value. Therefore, the measured value of ammonia-nitrogen is half that compared to conventional methods. This difference is accounted for by multiplication of the measured value by the coefficient K=2. The coefficient K changes according to the curve in FIG. 4 as the predetermined level of pH is changed.

We found at pH=9.25 that the mixed liquor has very little degradation, and ammonia released from the microorganisms is negligible and has essentially no influence on the ammonia measurement result in the range of measurements higher than 1 ppm ammonia. This is shown in Table 1.

TABLE 1

| Time the mixed liquor kept at pH = 9.25, in minutes | 10 min | 20 min | 30 min |
| --- | --- | --- | --- |
| Ammonia-nitrogen released from the microbes, in mg/liter | 0.02 | 0.07 | 0.16 |

Usually the time for an ammonia measurement is shorter than about 10 min. Therefore, the ammonia gas released from the microorganisms at pH=9.25 has a very minor, de minimus, influence on the measurement results. At higher pH, we discovered that the ammonia release rate from the sludge is significantly higher and this factor must be taken into consideration during the ammonia measurement. Otherwise, measurements are inaccurate. For example, from the mixed liquor with MLSS concentration 2500 mg/l, approximately 1 ppm of ammonia was released within 45 minutes at pH=10. At pH=11, it takes 30 minutes for 1 ppm of ammonia to be released.

Figure 5:
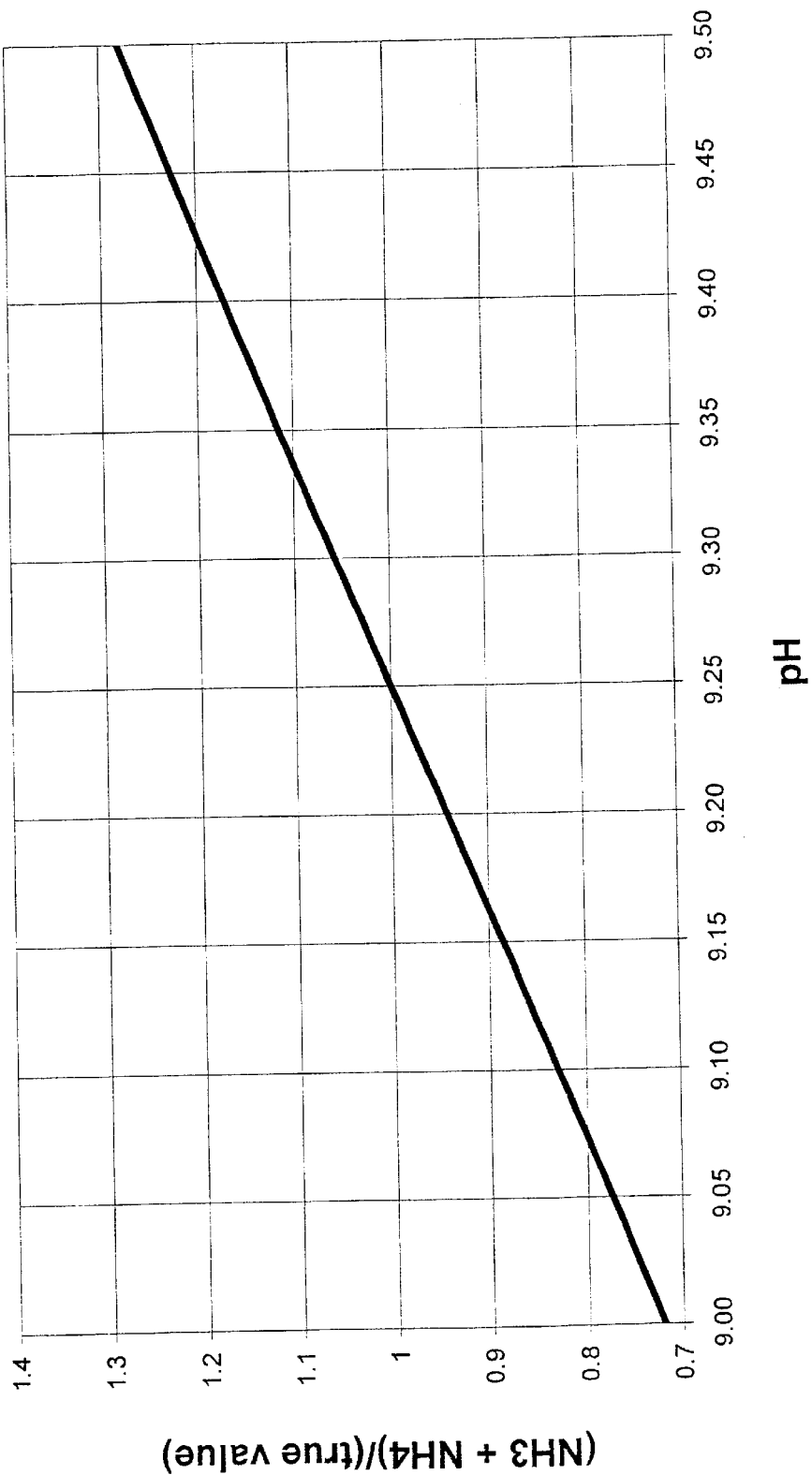
FIG. 5 is a graph of $(NH_3+NH_4^+)/(\text{true value})$ versus pH.

The second factor that has great influence on the accuracy of ammonia measurement is to maintain the pH steady at pH=9.25 during the ammonia measurement. This stability depends on the accuracy and stability of the pH meter and reply time of the pH probe (both these parameters depend on probe age). The stability of pH also depends on the accuracy of the system that delivers the base solution for adjustment of pH. Another factor that influences the ammonia measurement is the alkalinity of the mixed liquor. In order to obtain at least ±5% accuracy of ammonia measurement, the pH value should be kept in the range 9.25±0.05 as shown in FIG. 5.

Figure 6:
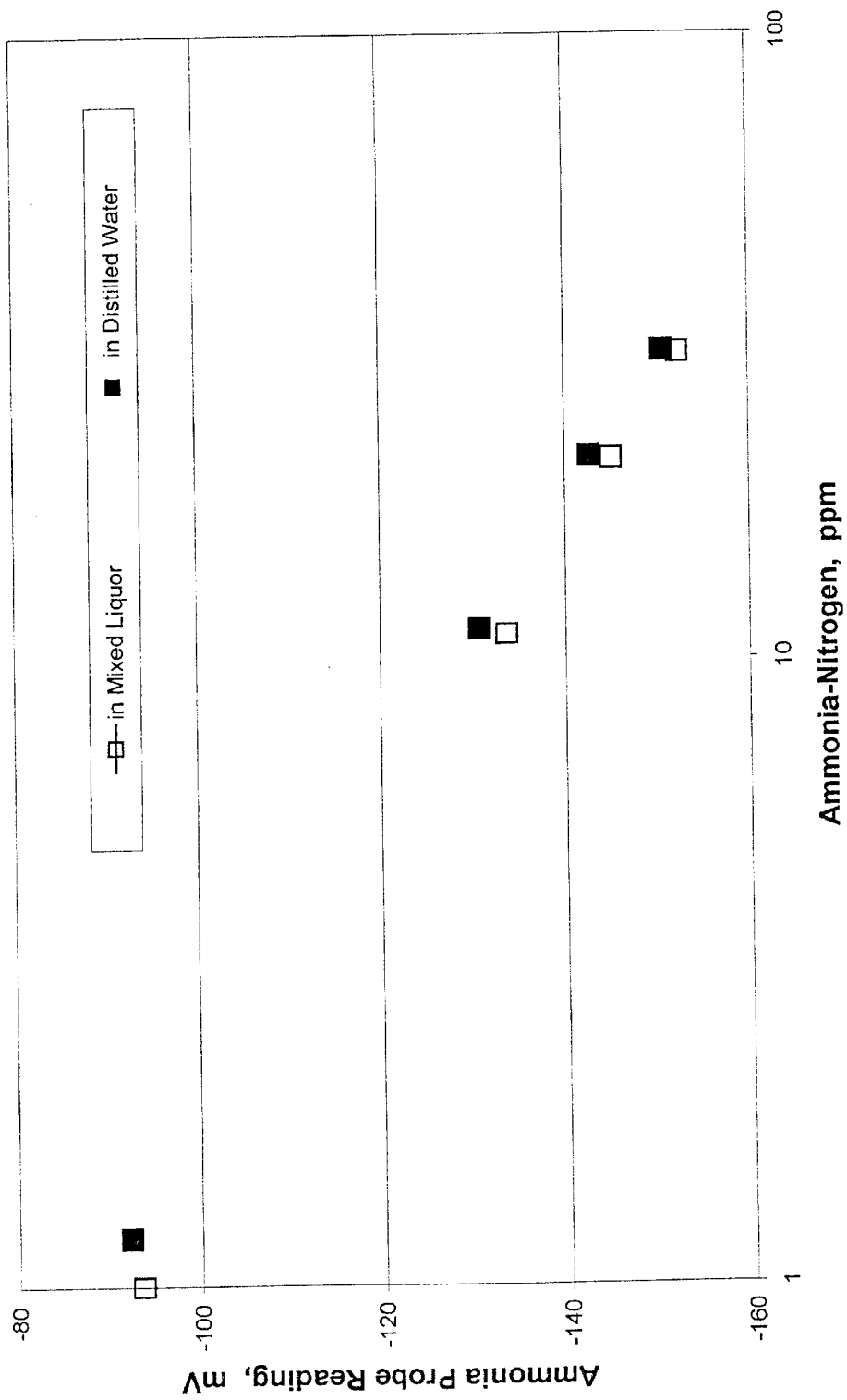
FIG. 6 is a graph of an ammonia probe reading in mV versus the amount of ammonia in ppm for an ammonia probe calibration. One calibration is conducted in mixed liquor and one in distilled water.
Figure 7:
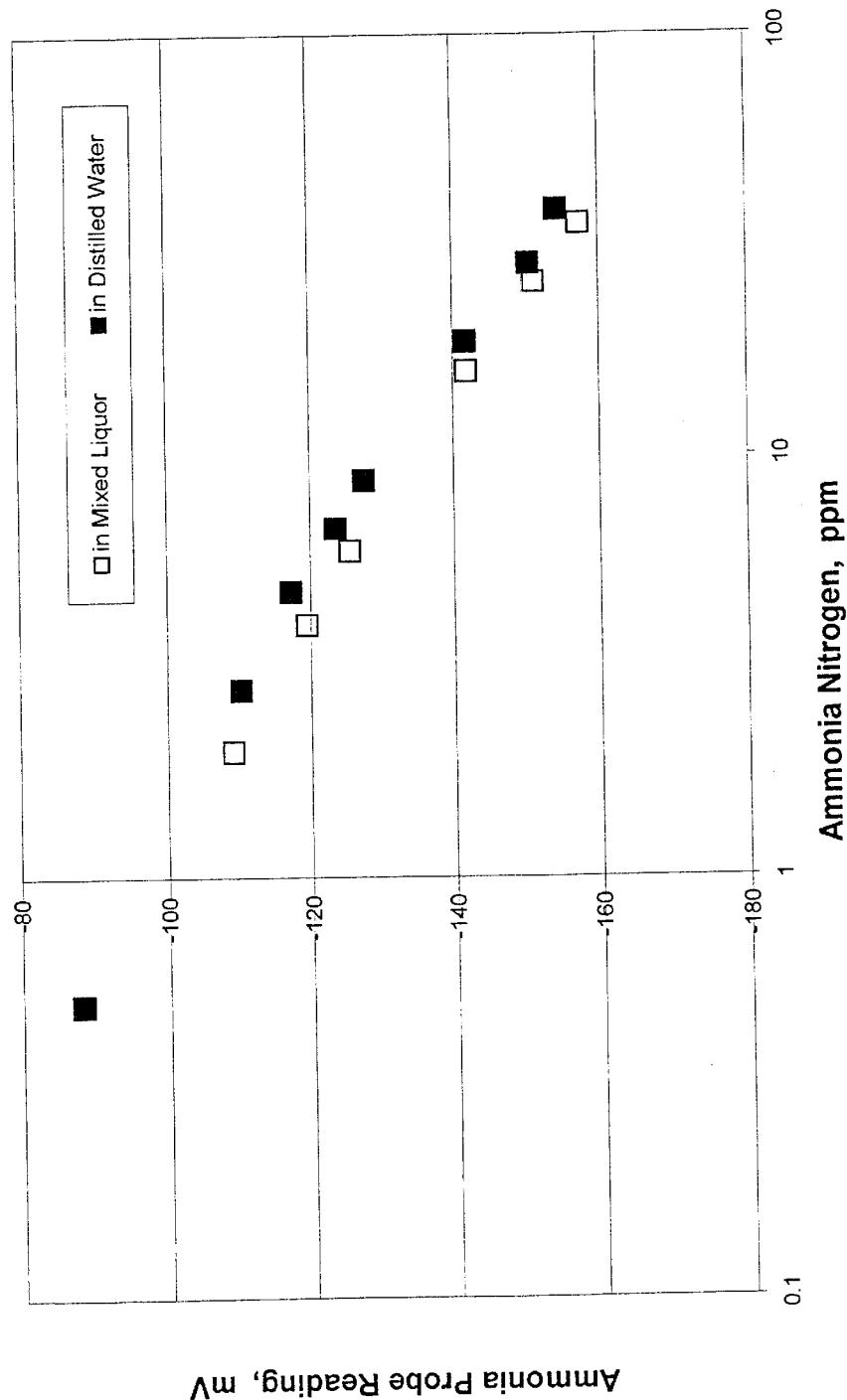
FIG. 7 is another graph of an ammonia probe reading in mV versus the amount of ammonia in ppm for an ammonia probe calibration. One calibration is conducted in mixed liquor and one in distilled water.

For practical application of the method in the wastewater industry the range of ammonia measurement should be in the range from about 0.1 to 40 ppm. We calibrated an automatic device for ammonia measurement both in distilled water and mixed liquor with MLSS concentration of 2500 mg/L. We discovered that the linear correlation between the signal value registered with the device and Log (NH3-N concentration) both in distilled water and mixed liquor was within the above-mentioned ammonia-N range. The calibration lines are presented in FIGS. 6 and 7. Unfortunately, there is some deviation between these two calibration graphs. Without being bound by theory, we believe that this might be caused by the different mobile activity of ammonia-gas molecules in different liquids. Therefore, we did not apply the calibration graph made in distilled water for ammonia measurements in mixed liquor. However, we made calibrations directly in mixed liquor and this deviation can be taken out from further consideration. The calibration performed directly in mixed liquor by a known ammonia amount addition may be different from the different pH at which the ammonia measurements are being performed. At pH=9.25 there is no need for compensation for possible ammonia gas release from the cells, because such release is negligible during the measurement time. However, to obtain high accuracy for measurements the pH of mixed liquor should be kept with an accuracy at least ±0.05 pH. On the other hand, measurements can be taken at pH=12 when all ammonia is converted to gas form. However, the ammonia release from the cells of microorganisms should be compensated by the measurement method.

Figure 8:
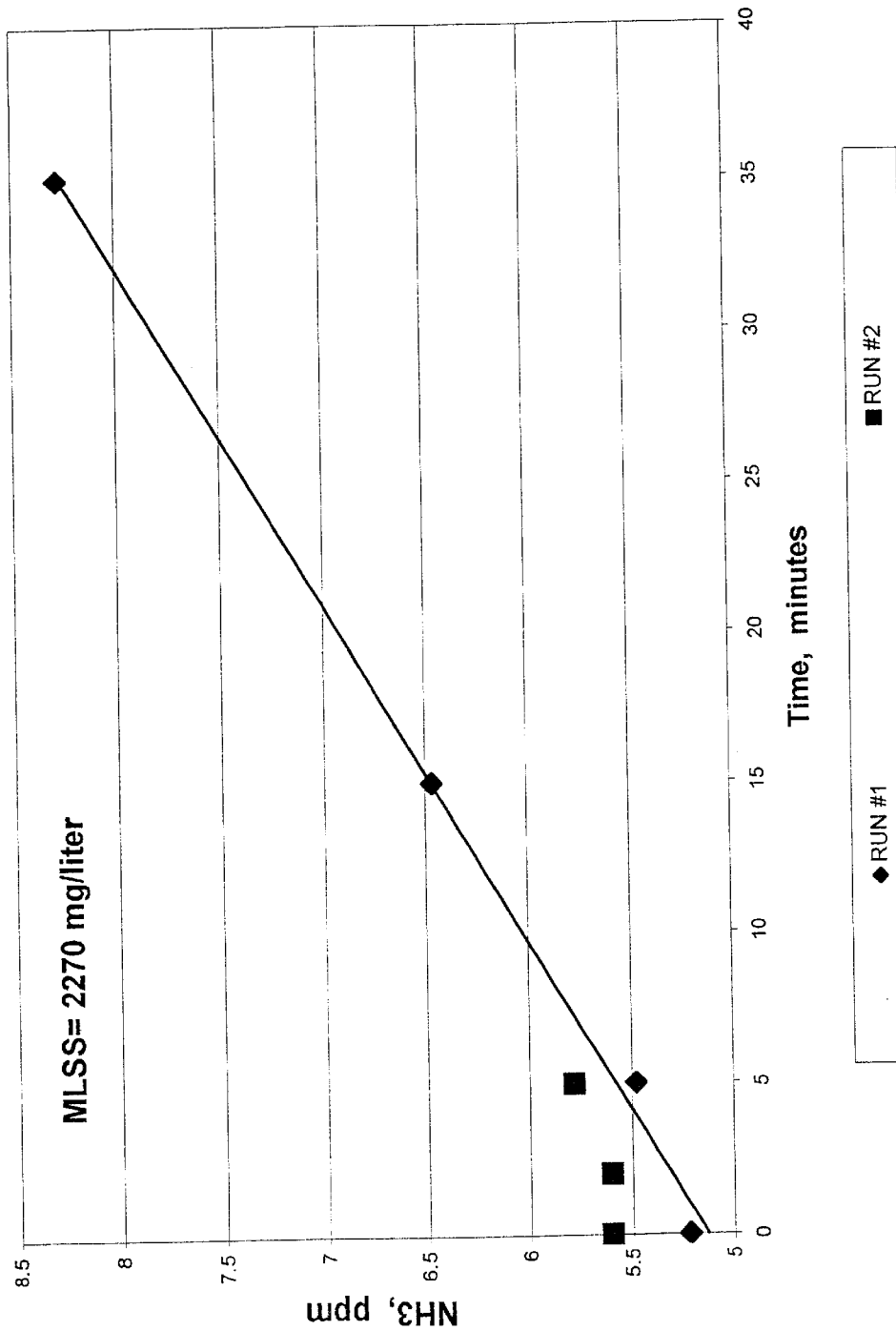
FIG. 8 is a graph of $NH_3$ in ppm versus time at pH=12 as ammonia is released from the cell body of the microorganisms. The release rate can be considered constant against time.

As described above, we found that ammonia is released from cell bodies in the mixed liquor aqueous medium at elevated pH level. Elevated pH is defined as about 10 or more, preferably about 12, most preferably 12. This is believed to be due to the hydrolysis of proteins on the cell walls or inside the cell bodies at high pH. Since the invention does not use biomass filtration, ammonia released from the biomass in the mixed liquor during ammonia measurement is a potential significant interfering factor in the measurement of ammonia in the sample and in the treatment tank. The amount of ammonia released to the water phase is dependent on the concentration and health of biomass, pH and temperature, among other factors. The phenomenon of this release of ammonia at pH=12 is shown in FIG. 8.

In determining the quantity of ammonia, the operator should decide a target pH at which to operate. When the pH is selected at a value lower than about 10, the effect of ammonia release is minimal as previously described. For example, pH=9.25 is maintained within a tight tolerance of ±0.05 by pumping a pH adjustment solution such as KOH into the sample chamber. At higher pH, above about 10, the release of ammonia gas is more prevalent and the pH tolerance need not be quite as high. However, the quantity of ammonia introduced into the mixed liquor due to ammonia release can significantly skew the measured quantity. This necessitates multiple measurements, all taken within short periods of time, to determine the actual measured ammonia quantity.

Ammonia concentration in the water phase can be analyzed by an ammonia gas sensor/probe when the pH of the water phase is adjusted to 11.5 or higher where more than 99% of ammonium ions ($NH_4^+$) are converted to free ammonia ($NH_3$). Conventional methods of ammonia analysis in wastewater samples require pre-treatment of the samples such as filtration and ionic strength adjustment. The purpose of wastewater sample filtration is to remove organic solids such as microorganisms and proteinaceous particles. Organic materials can be hydrolyzed in the water phase when the pH level is higher than 11. The hydrolysis of organic materials, especially proteinaceous compounds, releases ammonia to the water phase. During ammonia analysis, if the water sample is not filtered, the release of ammonia due to hydrolysis has heretofore caused inaccurate measurement of ammonia concentration in the water phase.

We discovered that an alternative way to sample filtration is to measure the ammonia release rate during the ammonia analysis and compensate the measured ammonia concentration according to the release rate. In this invention, the ammonia analyzer collects wastewater samples, in situ, and conducts ammonia analysis without filtration or removal of organic solids. By using a compensation method, the ammonia concentration is calculated from the signal (in mV) recorded by a conventional ammonia probe. Calibration of the ammonia probe is also conducted automatically with a similar method when calibration standard solution is introduced to the sample container.

In the following description, the time variables, $t_0$, $t_1$, $t_2$, $t_3$ and $t_4$ are measured from the moment of base injection to the sample container, in seconds. The signal from the ammonia probe is registered in mV and ammonia concentration is measured as $NH_3$-N mg/liter (ppm).

Figure 9:
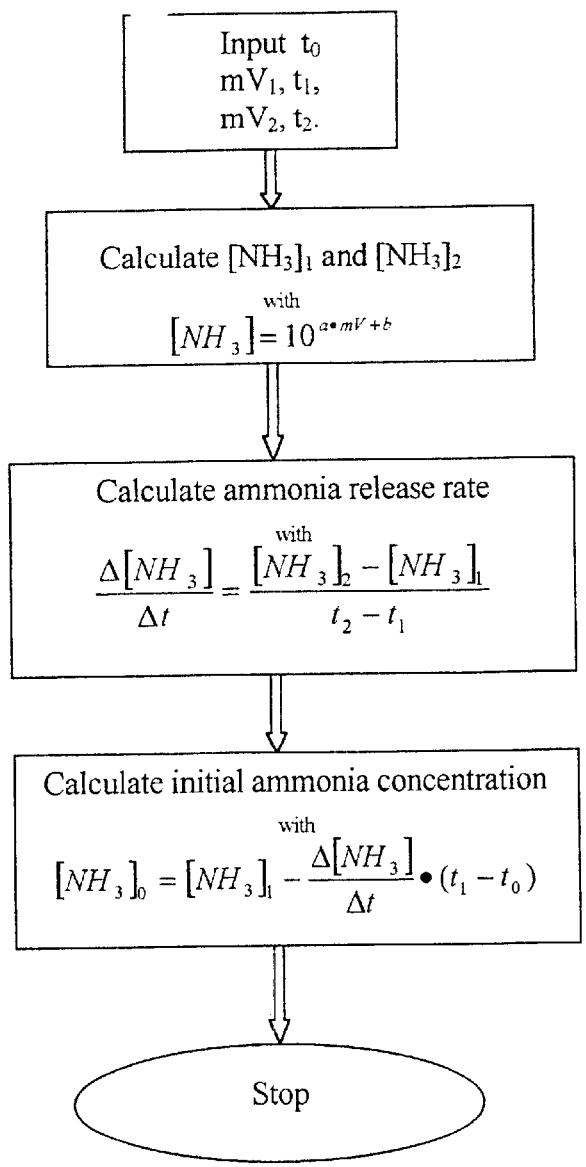
FIG. 9 is a block diagram of a method to measure ammonia in accordance with aspects of the invention.

The operation of the ammonia analyzer in the measurement mode is shown schematically in FIG. 9 and is as follows:

a) Collect a mixed liquor sample from the wastewater treatment tank.

b) Inject pH adjustment solution to bring the pH of the water phase to about 12.0. This can be done either through a predetermined amount or feedback control by way of a pH probe. This is recorded as time zero, $t_0$.

c) Wait to $t_1$ seconds to read the first $mV_1$ reading from the ammonia probe.

d) Wait to $t_2$ seconds to read the second $mV_2$ reading from the ammonia probe.

e) Use the following equation to calculate ammonia concentrations from $mV_1$ and $mV_2$, where a and b are linear coefficients of the ammonia probe.

$$[NH_3]=10^{a \cdot mV+b}$$

f) The amount of released ammonia from the sample up to the first $mV_1$ reading is calculated as:

$$\frac{\Delta [NH_3]}{\Delta t} = \frac{[NH_3]_2 - [NH_3]_1}{t_2 - t_1}$$

g) The ammonia concentration of the sample is calculated as:

$$[NH_3]_0 = [NH_3]_1 - \frac{\Delta [NH_3]}{\Delta t} \cdot (t_1 - t_0)$$

h) After the measurement of ammonia concentration, the sample is discharged to the treatment tank, and a fresh sample is taken for the next analysis.

Figure 10:
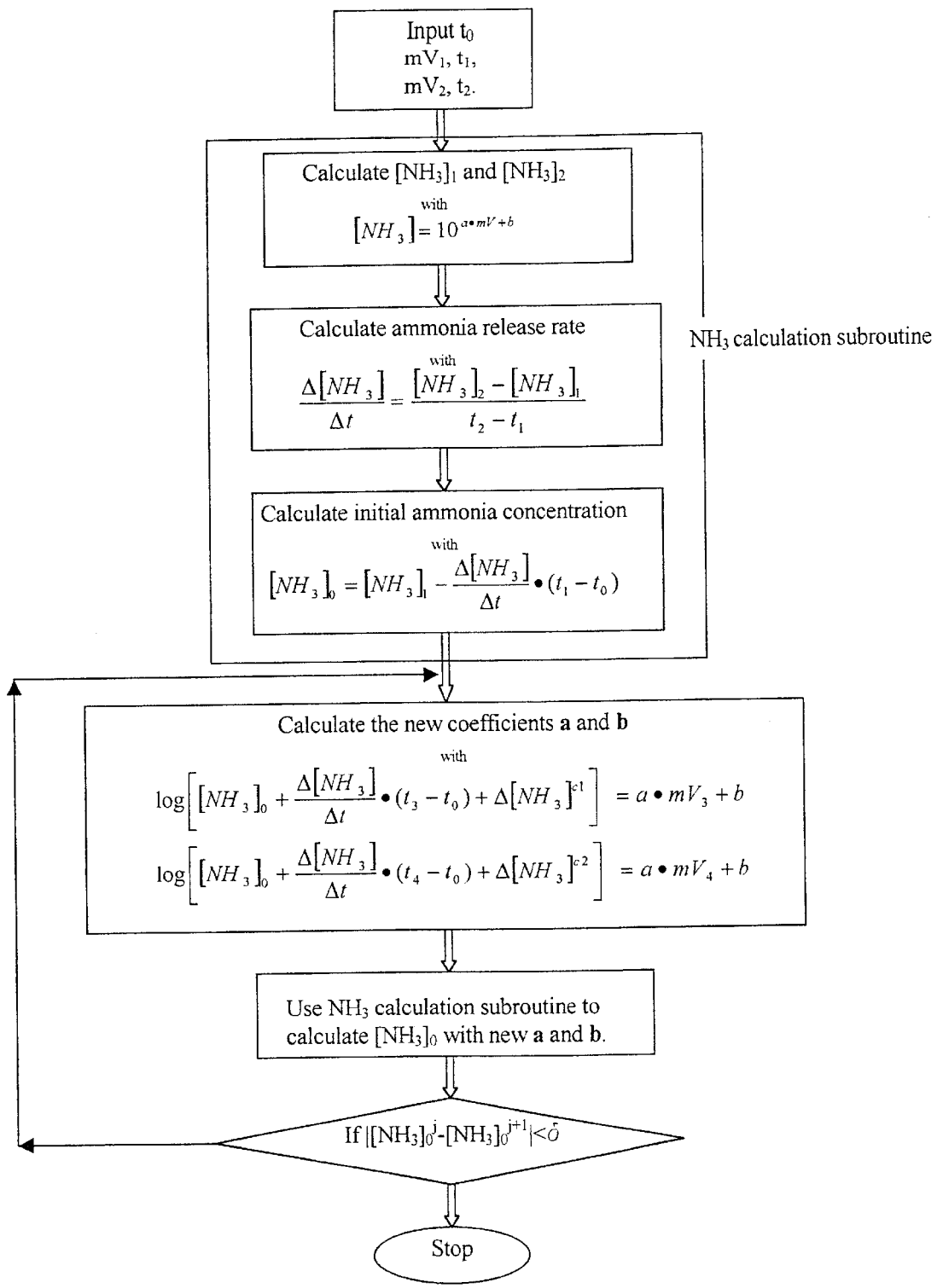
FIG. 10 is a block diagram of a method of calibrating the ammonia analyzer in accordance with aspects of the invention.

The ammonia analyzer can be calibrated according to the block diagram shown in FIG. 10 and according to the following method:

a) Collect a mixed liquor sample from the wastewater treatment tank and conduct ammonia analysis as described above, except that the sample is not discharged to the treatment tank after the ammonia concentration is measured. Parameters and intermediate results such as $[NH_3]_1$, $[NH_3]_2$, $mV_1$, $mV_2$, $\Delta[NH_3]/\Delta t$ are saved for use in the calibration step.

b) After the ammonia concentration is measured, a predetermined volume of ammonia solution is injected into the sample container so that the concentration of ammonia in the container increases by a $\Delta[NH_3]^{c1}$, (e.g. 0.5 ml of 1000 ppm $NH_4Cl$-N solution for $\Delta[NH_3]^{c1}=1$ ppm.)

c) Wait to $t_3$ seconds to read the third $mV_3$ reading from the probe.

d) Inject a second dose of calibration solution so that the concentration of ammonia increases by a $\Delta[NH_3]^{c2}$, (e.g. 2.0 ml of 1000 ppm $NH_4Cl$-N solution for $\Delta[NH_3]^{c2}=5$ ppm, taken into account of the first dose of calibration solution.)

e) Wait to $t_4$ seconds to read the fourth $mV_4$ reading from the probe.

f) Use the following equations to calculate the linear coefficients of ammonia, a and b:

$$\log[NH_3]_0 + \frac{\Delta[NH_3]}{\Delta t} \cdot (t_3 - t_0) + \Delta[NH_3]^{c1} = a \cdot mV_3 + b$$

$$\log[NH_3]_0 + \frac{\Delta[NH_3]}{\Delta t} \cdot (t_4 - t_0) + \Delta[NH_3]^{c2} = a \cdot mV_4 + b$$

g) Use the newly obtained a and b to calculate $[NH_3]_0$ from $mV_0$. If the newly calculated $[NH_3]_0$ substantially agrees with original $[NH_3]_0$, then the calibration is deemed successful, otherwise, use the newly calculated $[NH_3]_0$ to repeat the calibration process. The calibration is considered complete when the difference between $[NH_3]_0^j$ and $[NH_3]_0^{j+1}$ is within an acceptable, predetermined range.

h) Discharge the sample to the treatment tank and start a new measurement cycle.

i) The calibration of the ammonia analyzer can be performed as frequently as every measurement cycle, or everyday. The default calibration frequency is preferably once a day.

In accordance with the general teachings set forth above, several examples were conducted. Example 1 contains experimental data taken with a pH at an elevated level of 12.

EXAMPLE

Figure 11:
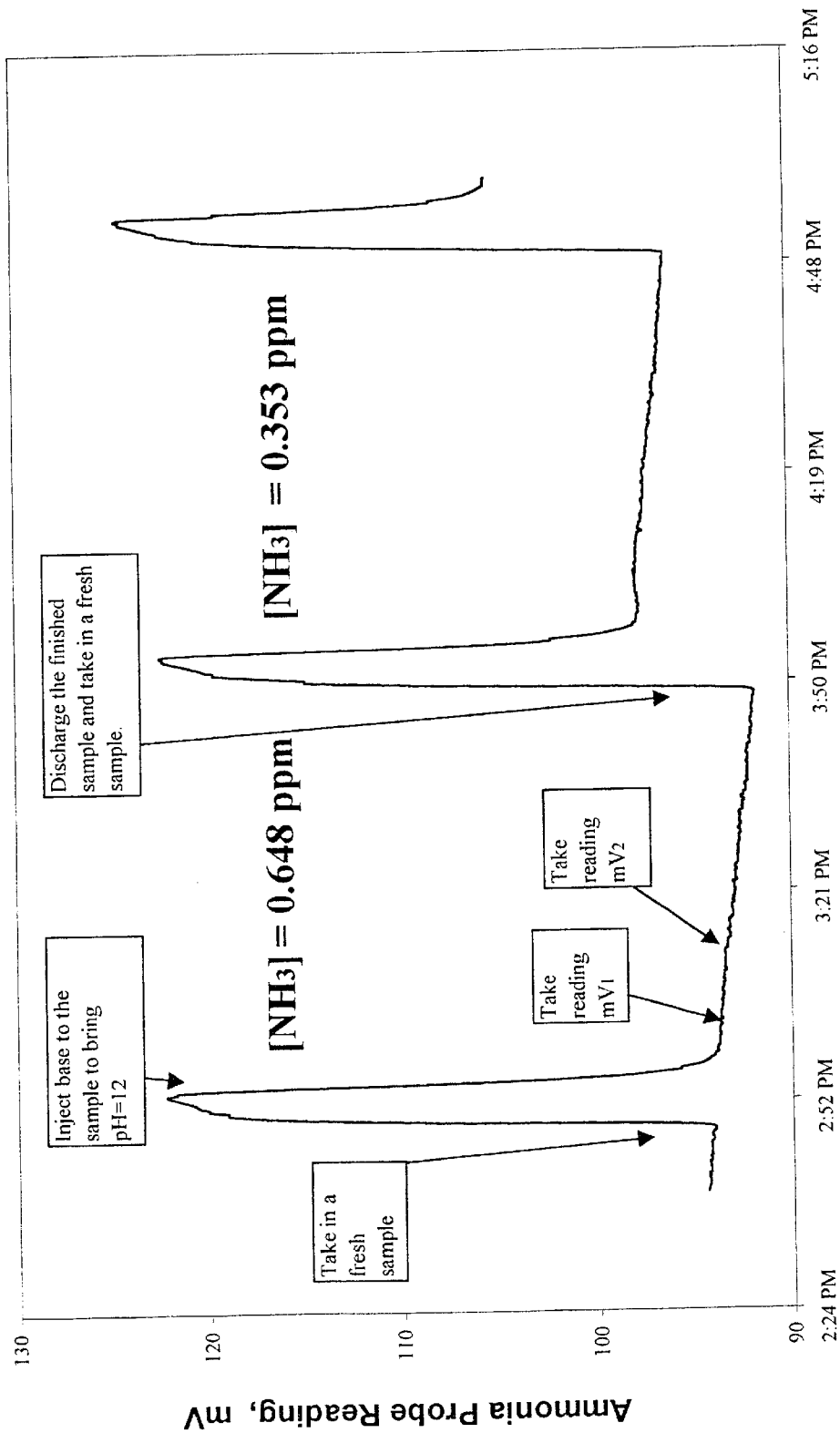
FIG. 11 is a graph of two cycles of on-line ammonia analysis utilizing the embodiments of the invention.

The apparatus for measuring ammonia was composed of one automatic sampler with the same configuration as the apparatus shown in FIG. 3 wherein sample container 8 had a capacity of 500 ml. After a fresh mixed liquor sample was captured in the sample container, approximately 1.0 ml of 10 N of KOH solution was introduced into the sample to bring the pH to 12.0±0.3. In this particular example, a pH probe is not needed. The volume of sample container 8 is known and it is, therefore, possible to add a known quantity of pH adjustment solution into chamber 8 that will automatically result in the desired pH=12±0.3. More than 99.9% of ammonia in the mixed liquor was in free form ($NH_3$) at this pH level. The ammonia gas probe measured the ammonia concentration within a short period of time as shown in FIG. 11. Table 2 lists the parameters and final results of the two ammonia analysis cycles.

TABLE 2

| Items | Cycle One | | Cycle Two | |
|---|---|---|---|---|
| | Time | $NH_3$—N ppm | Time | $NH_3$—N ppm |
| $t_0$ | 14:50 | 0.648 | 15:54 | 0.353 |
| $t_1$ | 15:02 | 0.686 | 16:08 | 0.392 |
| $t_2$ | 15:12 | 0.718 | 16:19 | 0.418 |
| $NH_3$ Release Rate, ppm-$NH_3$/min. | 0.00315 | | 0.00260 | |

Figure 12:
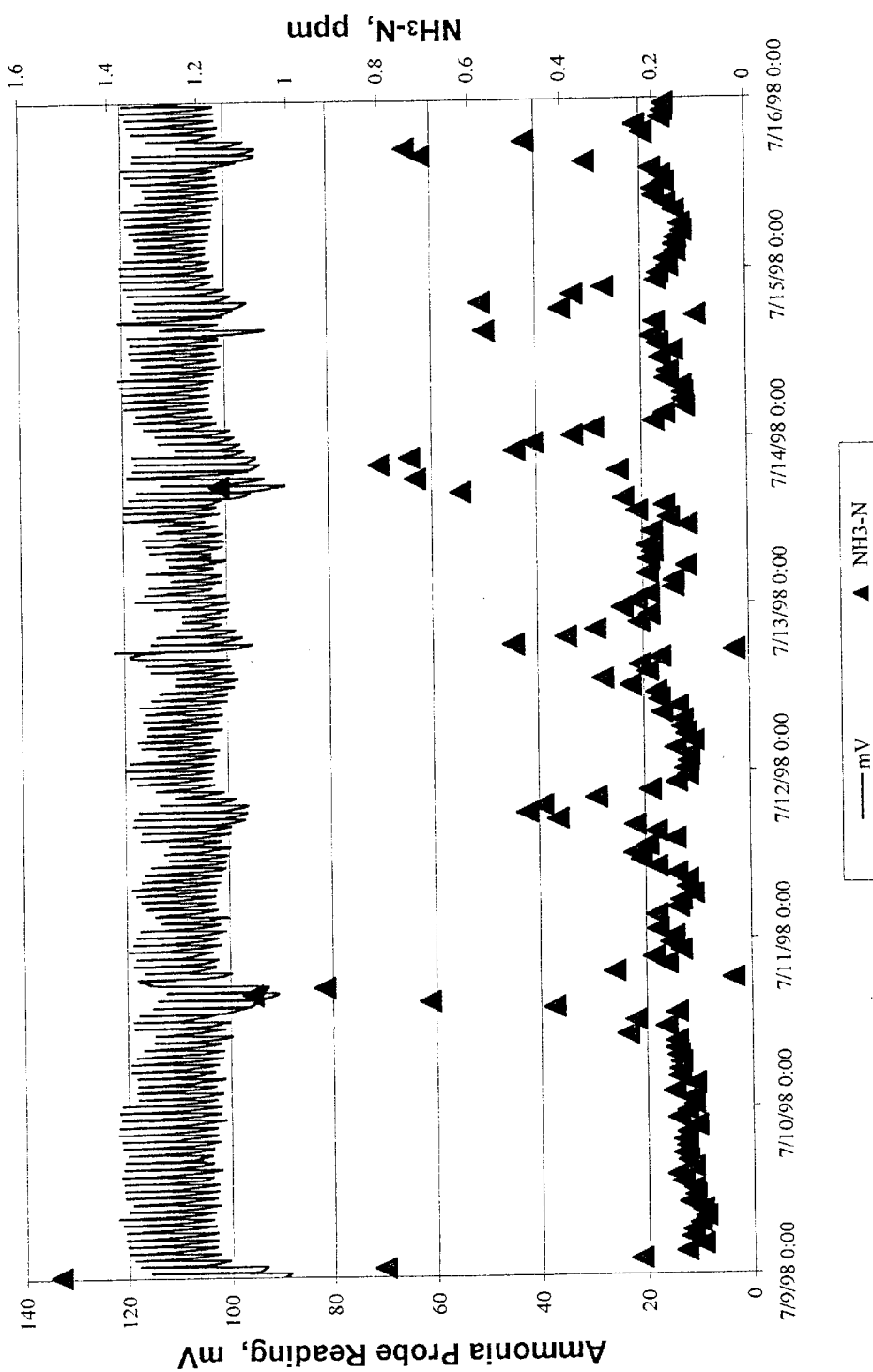
FIG. 12 is a graph of one week of on-line measurements of ammonia in an aeration basin at a full-scale wastewater treatment plant utilizing embodiments of the invention.

After the ammonia measurement, sample container 8 was opened to release the finished sample and capture a fresh sample for the next analysis. FIG. 12 shows a one-week on-line measurement of ammonia in an aeration basin in a full-scale wastewater treatment plant with the apparatus of the invention.

The ammonia probe was calibrated at given intervals in daily operation (from once per cycle to once per a day). In the calibration mode, after a fresh mixed liquor sample was taken into the container, the ammonia concentration was analyzed as a regular analysis cycle. In this example, the ammonia concentration in the mixed liquor sample was found to be 3.05 ppm, ($NH_3$=3.05 ppm). After the ammonia measurement, a given amount of ammonia solution was injected to the mixed liquor to bring an incremental change of ammonia concentration $\Delta[NH_3]^{c1}$ in the sample. In this example, $\Delta[NH_3]^{c1}=1.0$ ppm and $NH_3+\Delta[NH_3]^{c1}=4.05$ ppm. Then, another dose of ammonia solution was injected to the mixed liquor to bring one more incremental change in ammonia concentration $\Delta[NH_3]^{c2}$ in the sample. In this example, $\Delta[NH_3]^{c2}=5.0$ ppm and $NH_3+\Delta[NH_3]^{c1}=9.05$ ppm.

Figure 13:
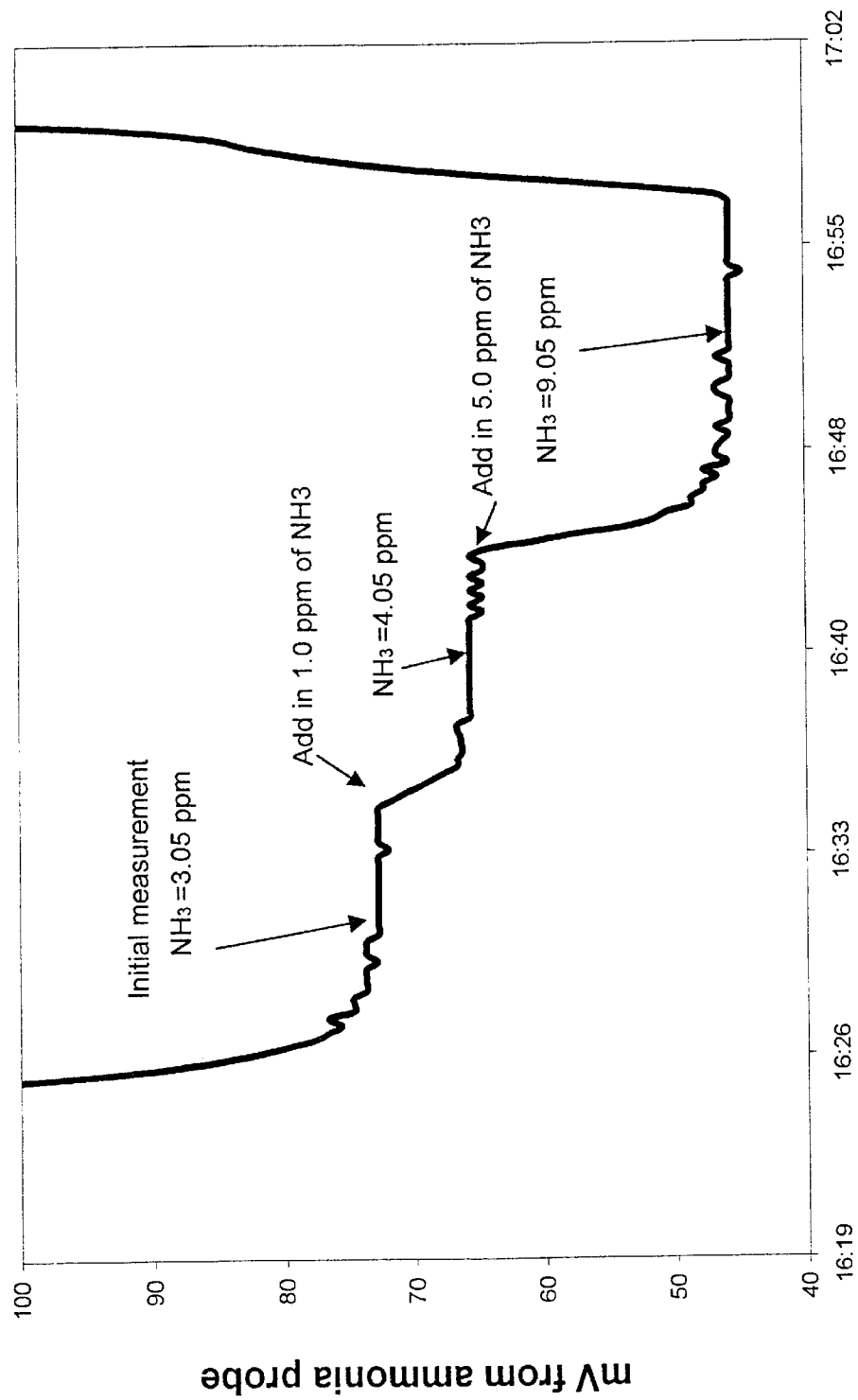
FIG. 13 is a graph of calibrating the ammonia analyzer.

The new coefficients of ammonia probe a and b were calculated with the formula described in step f) of the calibration procedure. Using the newly obtained a and b to calculate the initial concentration of ammonia (3.05 ppm). The probe was considered to be in good condition when the two measurements gave the same $NH_3$ value within an acceptable accuracy range. Otherwise, the analyzer would use the newly obtained a and b to calculate the initial ammonia concentration until the ammonia values from two consecutive calculations were within acceptable range. FIG. 13 shows a graph obtained in an analyzer calibration process.

One especially preferred application of the invention is to monitor ammonia concentration in a wastewater treatment process. The apparatus can be installed at the plant influent line to monitor the ammonia loading to the plant. The detection of high ammonia concentration in the influent will generate an alarm to warn the plant operator about the incoming ammonia loading. Increasing the mixed liquor concentration, increasing oxygen supplied to the aeration basin, or diverting a fraction of the influent to an equalization tank to avoid the peak loading are a few adjustments that can be done by the informed operators.

When the apparatus is installed in the final effluent line of a wastewater treatment plant, the plant can consistently monitor the ammonia concentration that is discharged. This will enable the operator to avoid exceeding the ammonia discharge limit, thus eliminating environmental pollution and penalties imposed by regulating agencies. More importantly, the apparatus of the invention can be installed in an aeration basin of a wastewater treatment plant to monitor and control the nitrification process. Mixed liquor concentration, oxygen supply rate, internal recycle flow rate, the number of aeration trains in operation, among other factors, can be regulated to achieve the desired nitrification at minimum operation cost.

Additionally, individual components of the invention may utilize equivalent substitutions. For example, the sample in detection chamber 8 may be uniformly suspended by use of any means of controllable agitation. The filling of the detection chamber with a predetermined amount of wastewater may be performed by other means. The monitoring system may consist of personal computer with applicable software or individual electronic meters to be analyzed separately, all of which are known in the art.

The pH probe in the apparatus may be eliminated when the apparatus is using an ammonia analyzing method at about pH=12 or higher. The delivery device 52 can be a separate unit or be integrated with the controller. The concentration of base solution and ammonia calibration solution can be varied so long as the amount of solution needed and delivered to sample chamber 8 are known.

What is claimed is:

1. A method of measuring ammonia in liquid comprising:
   a) isolating a liquid sample;
   b) adjusting the pH of said sample at time $t_0$;
   c) recording a value of ammonia present in said sample with an ammonia selective probe at a predetermined time $t_1$;
   d) recording another value of ammonia present in said sample after another predetermined time $t_2$;
   e) determining ammonia concentrations in said sample at each predetermined time $t_1$ and $t_2$ according to the following formula:

$$[NH_3] = 10^{a \cdot mV + b}$$

wherein a and b are linear coefficients of the ammonia probe;
   f) determining the amount of released ammonia from said sample according to the following formula:

$$\frac{\Delta [NH_3]}{\Delta t} = \frac{[NH_3]_2 - [NH_3]_1}{t_2 - t_1}; \text{ and}$$

g) determining the ammonia concentration of the sample according to the following formula:

$$[NH_3]_0 = [NH_3]_1 - \frac{\Delta [NH_3]}{\Delta t} \cdot (t_1 - t_0).$$

2. The method defined in claim 1 further comprising discharging said sample and repeating steps a)–g).

3. The method defined in claim 1 further comprising periodically calibrating said ammonia selective probe.

4. The method defined in claim 3 wherein said calibrating comprises:
   h) injecting a predetermined volume of calibration solution into the sample to increase the concentration of ammonia in the sample by $\Delta[NH_3]^{c1}$;
   i) recording a calibration value $mV_3$ of ammonia present in said sample at time $t_3$;
   j) injecting another predetermined volume of calibration into the sample to increase the concentration of ammonia by $\Delta[NH_3]^{c2}$;
   k) recording another calibration value $mV_4$ of ammonia present in said sample at time $t_4$;
   l) determining the linear coefficients of ammonia, a and b according to the following formulae:

$$\log[NH_3]_0 + \frac{\Delta [NH_3]}{\Delta t} \cdot (t_3 - t_0) + \Delta [NH_3]^{c1} = a \cdot mV_3 + b$$

$$\log[NH_3]_0 + \frac{\Delta [NH_3]}{\Delta t} \cdot (t_4 - t_0) + \Delta [NH_3]^{c2} = a \cdot mV_4 + b;$$

m) using a and b, determining $[NH_3]_0$ from $mV_1$;
   n) comparing $[NH_3]_0$ obtained from step g) to $[NH_3]_0$ obtained from step m);
   o) determining that said ammonia selective probe is calibrated when $[NH_3]_0$, when obtained from step g) and $[NH_3]_0$, obtained from step m) are substantially similar.

5. The method defined in claim 1 wherein said pH predetermined level is between about 6 and about 12.

6. The method defined in claim 1 wherein said pH predetermined level is about 9.25.

7. The method defined in claim 1 wherein said pH predetermined level is about 12.0.

8. The method defined in claim 1 wherein said pH predetermined level has a tolerance of about ±0.01.

9. The method defined in claim 1 wherein said pH predetermined level has a tolerance of about ±0.3.

10. The method defined in claim 1 wherein said liquid contains organic matter.

11. The method defined in claim 1 wherein at least a portion of said organic matter is capable of releasing ammonia.

12. The method defined in claim 1 wherein said liquid is unfiltered.

13. The method defined in claim 1 wherein said liquid is wastewater.

* * * * *